US012533477B2

(12) United States Patent
Himura et al.

(10) Patent No.: US 12,533,477 B2
(45) Date of Patent: Jan. 27, 2026

(54) HOLLOW NEEDLE

(71) Applicant: FURUKAWA ELECTRIC CO., LTD., Tokyo (JP)

(72) Inventors: Atsushi Himura, Tokyo (JP); Takeshi Yagi, Tokyo (JP); Kazutaka Nara, Tokyo (JP); Katsuki Suematsu, Tokyo (JP); Tsunenori Arai, Tokyo (JP)

(73) Assignee: FURUKAWA ELECTRIC CO., LTD., Tokyo (JP)

( * ) Notice: Subject to any disclaimer, the term of this patent is extended or adjusted under 35 U.S.C. 154(b) by 811 days.

(21) Appl. No.: 17/906,036

(22) PCT Filed: Jan. 15, 2021

(86) PCT No.: PCT/JP2021/001306
§ 371 (c)(1),
(2) Date: Sep. 9, 2022

(87) PCT Pub. No.: WO2021/181869
PCT Pub. Date: Sep. 16, 2021

(65) Prior Publication Data

US 2023/0023384 A1 Jan. 26, 2023

(30) Foreign Application Priority Data

Mar. 11, 2020 (JP) ................................ 2020-041995

(51) Int. Cl.
*A61M 5/32* (2006.01)

(52) U.S. Cl.
CPC .......... *A61M 5/3286* (2013.01); *A61M 5/329* (2013.01)

(58) Field of Classification Search
CPC ............................ A61M 5/3286; A61M 5/329
See application file for complete search history.

(56) References Cited

U.S. PATENT DOCUMENTS 5,702,352 A 12/1997 Kimura et al.
8,628,475 B2 1/2014 Wang
(Continued)

FOREIGN PATENT DOCUMENTS

EP 2 732 849 A1 5/2014
EP 10-2072634 B1 2/2020
(Continued)

OTHER PUBLICATIONS

Combined Chinese Office Action and Search Report issued May 11, 2024 in Chinese Patent Application No. 202180007179.1 (with unedited computer-generated English translation), 15 pages.
(Continued)

*Primary Examiner* — Dung T Ulsh
(74) *Attorney, Agent, or Firm* — Oblon, McClelland, Maier & Neustadt, L.L.P.

(57) ABSTRACT

A hollow needle includes a needle body made of an electrically conductive material, forming a cylindrical shape, and including a shaft part, a tip part connected with the shaft part, and an opening for discharging or drawing in a liquid in which a cavity communicating between the shaft part and the opening is formed. Also included is an annular insulating film made of an electrically insulative material, which exposes the opening and at least part of the tip part, and coats at least part of an outer circumferential surface of the shaft part.

19 Claims, 7 Drawing Sheets

(56) References Cited

U.S. PATENT DOCUMENTS

| | | | | |
|---|---|---|---|---|
| 2008/0228109 | A1 | 9/2008 | Kinoshita et al. | |
| 2014/0005592 | A1 | 1/2014 | Kim et al. | |
| 2017/0164881 | A1 | 6/2017 | Fujita et al. | |
| 2017/0252526 | A1 * | 9/2017 | Fox | A61B 17/3403 |
| 2021/0307716 | A1 * | 10/2021 | Stapert | A61B 17/3403 |

FOREIGN PATENT DOCUMENTS

| | | | |
|---|---|---|---|
| JP | 51-84291 | U | 7/1976 |
| JP | 8-150149 | A | 6/1996 |
| JP | 2004-242936 | A | 9/2004 |
| JP | 2005-205002 | A | 8/2005 |
| JP | 2006-296444 | A | 11/2006 |
| JP | 2008-79868 | A | 4/2008 |
| JP | 2008-237620 | A | 10/2008 |
| JP | 2008-264498 | A | 11/2008 |
| JP | 2017-108763 | A | 6/2017 |
| KR | 10-2012-0127917 | A | 11/2012 |

OTHER PUBLICATIONS

Combined Chinese Office Action and Search Report issued May 31, 2023 in Patent Application No. 202180007179.1 (with English machine translation), 17 pages.
Office Action issued Feb. 20, 2024, in corresponding Japanese Patent Application No. 2020-041995 (with English Translation), 6 pages.
Office Action issued Feb. 24, 2024, in corresponding Chinese Patent Application No. 202180007179.1 (with English Translation), 13 pages.
International Search Report issued Feb. 22, 2021 in PCT/JP2021/001306 filed Jan. 15, 2021, therein 6 pages.
Extended European Search Report issued Mar. 22, 2024 in European Patent Application No. 21766909.2, 7 pages.
Japanese Office Action issued Sep. 26, 2023 in Japanese Application 2020-041995, (with unedited computer-generated English translation), 7 pages.

* cited by examiner

HOLLOW NEEDLE

TECHNICAL FIELD

The present disclosure relates to a hollow needle.

BACKGROUND ART

Patent Document 1 discloses an electrode needle to be punctured into a living body, including a columnar or tubular core, an electrode formed in the core, an insulation part where the electrode is covered with insulative material, and an electrode window part where the electrode or a sensing layer formed on the electrode is exposed. With Patent Document 1, it is possible to measure information of glucose, by puncturing the electrode needle of about 5 mm length into subcutaneous tissue.

When obtaining information inside of a living body as mentioned above, a dedicated tool or device is used. Such a dedicated tool or device obtains only information inside of the living body. For this reason, after performing the procedure for obtaining information inside of the living body, it is necessary to separately perform a procedure such as injection of a drug solution into the living body or extraction of body fluids such as blood from inside the living body, using a tool separate from the dedicated tool or device. The damage to the living body tends to increase as the number of such procedures to the living body increases.

Patent Document 1: Japanese Unexamined Patent Application, Publication No. 2017-108763

DISCLOSURE OF THE INVENTION

Problems to be Solved by the Invention

On the other hand, the needle used in puncturing of the living body may have an opening for injecting a drug solution into the living body, and for extracting blood. Upon puncturing this type of hypodermic needle to a living body, it is desirable to configure so as to be able to recognize the position of the opening of the hypodermic needle, or the position of the tip from outside of the living body.

An object of the present disclosure is to provide a hollow needle enabling procedures such as injection of a drug solution into a living body and extraction of body fluids from the living body, and enabling recognition of the position of an opening or the position of the tip within the living body from outside the living body.

Means for Solving the Problems

A hollow needle according to a first aspect of the present invention includes: a needle body made of an electrically conductive material, forming a cylindrical shape, and including a shaft part, a tip part connected with the shaft part, and an opening for discharging or drawing in a liquid, wherein a cavity communicating between the shaft part and the opening is formed inside; and an annular insulating film made of an electrically insulative material, which exposes the opening and at least part of the tip part, and coats at least part of an outer circumferential surface of the shaft part.

According to a second aspect of the present invention, in the hollow needle as described in the first aspect, at least part of an outer circumferential surface of the tip part is electrically conductive, and is electrically connected to the shaft part.

According to a third aspect of the present invention, in the hollow needle as described in the first or second aspect, a maximum value for a step height h1 from the outer circumferential surface of the shaft part until a surface of the insulating film at an end position on a side of the tip part of the insulating film is 200 μm or less.

According to a fourth aspect of the present invention, the hollow needle as described in any one of the first to third aspects further includes, at an end on a side of the tip part of the insulating film, a gradually decreasing part for which a film thickness of the insulating film gradually decreases toward the tip part.

According to a fifth aspect of the present invention, in the hollow needle as described in any one of the first to fourth aspects, the needle body includes a recessed part with a decreased thickness on at least part of the outer circumferential surface of the shaft part, and the insulating film is accommodated in the recessed part of the shaft part.

According to a sixth aspect of the present invention, in the hollow needle as described in any one of the first to fifth aspects, a surface roughness Ra of a coated surface of the shaft part which is coated with the insulating film is more than 0 μm and 1 μm or less.

According to a seventh aspect of the present invention, in the hollow needle as described in any one of the first to sixth aspects, a surface roughness Ra of an uncoated surface of the shaft part which is not coated with the insulating film is smaller than a surface roughness Ra of the coated surface of the shaft part which is coated with the insulating film.

According to an eighth aspect of the present invention, in the hollow needle as described in any one of the first to seventh aspects, the shaft part slopes or bends toward the tip part, and the opening is formed at the tip part.

According to a ninth aspect of the present invention, in the hollow needle as described in any one of the first to eighth aspects, the insulating film is configured from a resin having an electrical insulating property.

According to a tenth aspect of the present invention, in the hollow needle as described in any one of the first to ninth aspects, the insulating film is configured from a polyimide resin or a fluorocarbon resin.

According to an eleventh aspect of the present invention, in the hollow needle as described in any one of the first to tenth aspects, the needle body is configured from a metal.

According to a twelfth aspect of the present invention, in the hollow needle as described in any one of the first to eleventh aspects, the needle body is configured from a stainless steel, a titanium alloy or a cobalt/molybdenum-containing alloy.

Effects of the Invention

According to the present disclosure, it is possible to provide a hollow needle enabling procedures such as injection of a drug solution into a living body and extraction of body fluids from the living body, and enabling recognition of the position of an opening or the position of the tip within the living body from outside the living body.

PREFERRED MODE FOR CARRYING OUT THE INVENTION

Hereinafter, an embodiment will be explained in detail.

Figure 1:
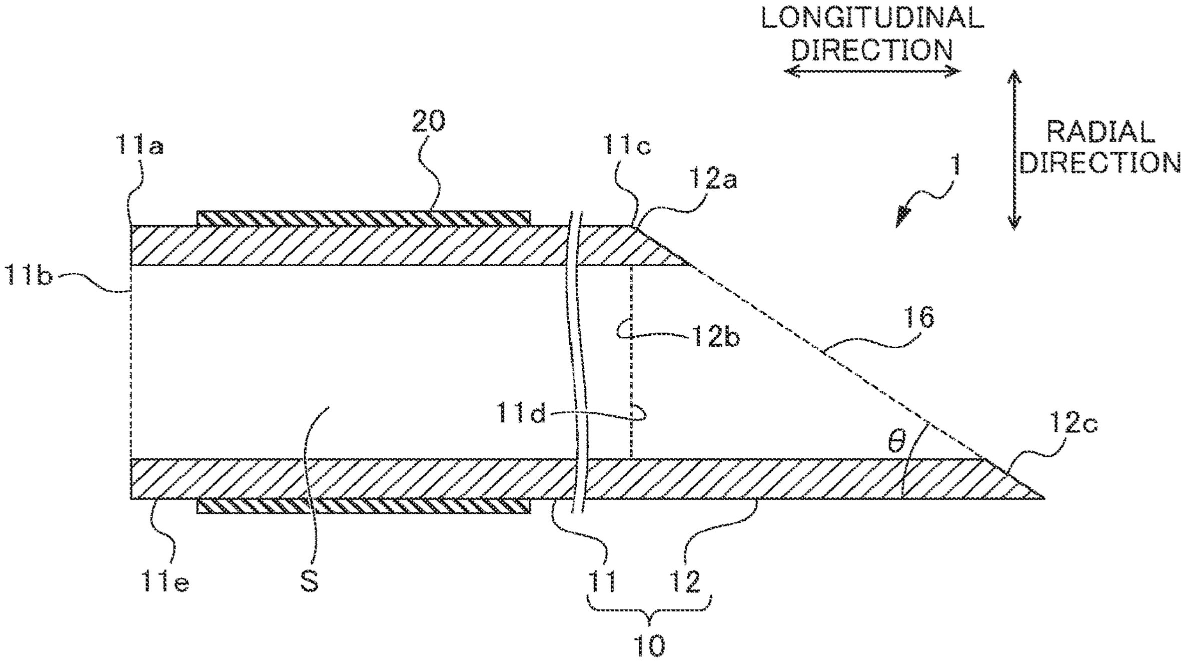
FIG. 1 is a longitudinal sectional view showing an example of a hollow needle according to an embodiment.

FIG. 1 is a longitudinal sectional view showing an example of a hollow needle according to an embodiment.

As shown in FIG. 1, a hollow needle 1 according to the embodiment includes a needle body 10 forming a cylindrical shape and having a shaft part 11, a tip part 12 connected with the shaft part 11, and an opening 16 for discharging or drawing in a liquid, in which a cavity S communicating between the shaft part 11 and the opening 16 is formed inside, the needle body 10 being made of an electrically conductive material; and an annular insulating film 20 made of an electrically insulative material, which exposes the opening 16 and at least part of the tip part 12, and coats at least part of an outer circumferential surface 11*e* of the shaft part 11. It should be noted that the insulating film 20 is integral and inseparable from the hollow needle 1, and thus not divided.

The hollow needle 1 has the needle body 10 and the insulating film 20. The shaft part 11 constituting the needle body 10 forms a cylindrical shape, and extends along the longitudinal direction of the hollow needle 1. An opening 11*b* on the base end side (hereinafter simply called opening lib) is provided to the base end 11*a* of the shaft part 11. The base end 11*a* of the shaft part 11 corresponds to the base end of the hollow needle 1. The opening 11*b* of the base end 11*a* of the shaft part 11 corresponds to the opening of the base end of the hollow needle 1. An opening 11*d* on the tip side (hereinafter simply called opening 11*d*) is provided to a tip 11*c* of the shaft part 11.

The shaft part 11 connects with the tip part 12. A base end 12*a* of the tip part 12 is integrally coupled to the tip 11*c* of the shaft part 11. An opening 12*d* on the base end side (hereinafter simply called opening 12*b*) is provided to the base end 12*a* of the tip part 12. The opening 11*d* of the tip 11*c* of the shaft part 11 communicates with the opening 12*d* of the base end 12*a* of the tip part 12. The tip part 12 assuming a cylindrical shape is formed so as to extend along the longitudinal direction of the hollow needle 1. The tip 12*c* of the tip part 12 corresponds to the tip of the hollow needle 1.

The opening 16 is provided to the needle body 10. The opening 16 discharges or draws in a liquid. Herein, as shown in FIG. 1, the opening 16 is provided to the side of the tip 12*c* of the tip part 12. It should be noted that the opening 16 has a shape such that cuts the tip part 12 obliquely relative to the longitudinal direction, i.e. cross-sectional shape of the opening 16 in which the length in the longitudinal direction from the base end 12*a* to the tip 12*c* of the tip part 12 gradually increases, is elliptical; however, it may be configuration in a different shape from this.

Inside of the needle body 10, a cavity S communicating between the shaft part 11 and the opening 16, and extending in the longitudinal direction of the hollow needle 1 is formed. The cavity S provided inside of the needle body 10 communicates from the opening 11*b* of the base end 11*a* of the shaft part 11 until the opening 16. A drug solution and body fluid injected or extracted by the hollow needle 1 flows in the cavity S.

The needle body 10 consists of an electrically conductive material. In other words, the shaft part 11 and the tip part 12 constituting the needle body 10 consist of an electrically conductive material. It should be noted that it may be configured so as to plate the needle body 10 with an electrically conductive material.

The needle body 10 is preferably configured from metal, and thereamong, it is more preferably configured from a stainless steel, a titanium alloy or a cobalt/molybdenum-containing alloy. If the needle body 10 is configured from metal, the electrical conductivity and the mechanical strength of the needle body 10 will be favorable, and the production of the needle body 10 will be easy. Furthermore, if the needle body 10 is configured from a stainless steel, a titanium alloy or a cobalt/molybdenum-containing alloy, in addition to the above-mentioned properties, the long-term stability such as rust prevention of the needle body 10 will improve.

The insulating film 20 consisting of an electrical insulative material exposes the opening 16 and at least part of the tip part 12, and annularly coats at least part of the outer circumferential surface 11*e* of the shaft part 11. As mentioned above, the tip part 12 consists of an electrically conductive material. The opening 16 and at least part of the outer circumferential surface of the tip part 12 are not coated with the insulating film 20. The opening 16 and at least part of the outer circumferential surface of the tip part 12 have electrical conductivity, and are electrically connected to the shaft part 11.

The insulating film 20 is preferably configured from a resin having electrical insulating property, and thereamong, it is more preferably configured from a polyimide resin or a fluorocarbon resin. If the insulating film 20 is configured from a resin having electrical insulating property, the electrical insulating property of the insulating film 20 will be favorable, and the film formation of the insulating film 20 on the needle body 10 is easy. Furthermore, when the insulating film 20 is configured from a polyimide resin or a fluorocarbon resin, in addition to the above-mentioned characteristics, the frictional coefficient of the surface of the insulating film 20 declines, and the mechanical strength of the insulating film 20 improves.

Regarding the average film thickness of the insulating film 20, the lower limit value is preferably 0.1 μm or more, more preferably 1 μm or more, and even more preferably 5 μm or more, and the upper limit value is preferably 100 μm or less, more preferably 30 μm or less, and even more preferably 10 μm or less. If the average film thickness of the insulating film 20 is 0.1 μm or more, the electrical insulating property of the insulating film 20 will be favorable. If the average film thickness of the insulating film 20 is 100 μm or less, the film formation of the insulating film 20 will be easy, and the outside diameter dimension in the radial direction of the hollow needle 1 will be small; therefore, it is possible to insert the hollow needle 1 smoothly into a living body.

For the length dimension in the longitudinal direction of the hollow needle 1, the lower limit value is preferably 15 mm or more, more preferably 20 mm or more, and even more preferably 25 mm or more, and the upper limit value is preferably 100 mm or less, more preferably 55 mm or less, and even more preferably 35 mm or less. If the length dimension of the hollow needle 1 is 15 mm or more, it is possible to easily insert the hollow needle 1 to the desired depth in the living body. If the length dimension of the hollow needle 1 is 100 mm or less, the handling property of the hollow needle 1 will be favorable.

For the outside diameter dimension in the radial direction of the hollow needle 1, the lower limit value is preferably 700 μm or more, more preferably 800 μm or more, and even more preferably 900 μm or more, and the upper limit value is preferably 1300 μm or less, more preferably 1100 μm or less, and even more preferably 1000 μm or less. If the outside diameter dimension of the hollow needle 1 is 700 μm or more, the hollow needle 1 can inject and extract a sufficient amount of drug solution or body fluid, and it is possible to raise the safety during false puncture. If the outside diameter dimension of the hollow needle 1 is 1300 μm or less, the lateral rigidity of the hollow needle 1 improves, and it is possible to linearly insert without bending, and possible to smoothly insert into a living body.

For the hollow needle 1 having such a needle body 10 and an insulating film 20, when voltage is applied between the outer circumferential surface 11*e* of the shaft part 11 and the outer circumferential surface of the tip part 12 which are not coated with the insulating film 20, electrical current flows between the shaft part 11 and the tip part 12 of the needle body 10, without flowing in a portion of the insulating film 20 coating the shaft part 11.

Figure 2:
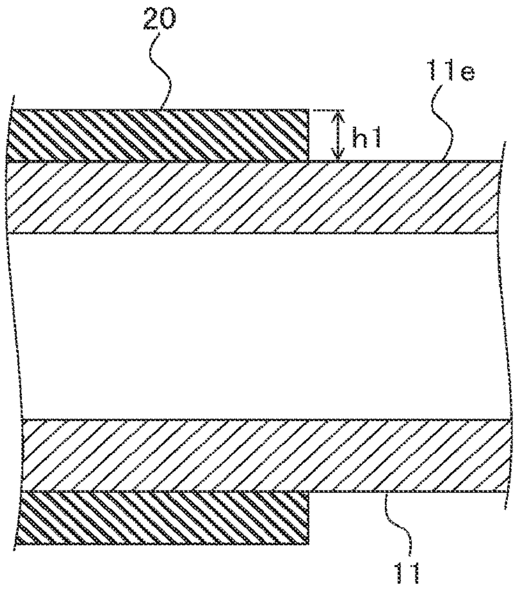
FIG. 2 is an enlarged cross-sectional view showing an example of a boundary between a shaft part and an end on a tip side of an insulating film in FIG. 1.

FIG. 2 is an enlarged cross-sectional view showing an example of a boundary between the shaft part 11 and the end on the tip side of the insulating film 20 in FIG. 1. The tip side of the insulating film 20 corresponds to the tip part side of the hollow needle 1. At an end position on the tip side of the insulating film 20, the maximum value for the step height h1 from the outer circumferential surface 11*e* of the shaft part 11 until the surface of the insulating film 20 is preferably 200 μm or less, and more preferably 100 μm or less. If the maximum value for the step height h1 at the annular end position is 200 μm or less, it is possible to smoothly insert the hollow needle 1 into a living body. Using a laser microscope (non-contact), it is possible to measure the maximum value for the step height h1. It should be noted that AFM (atomic force microscopy) or SEM (scanning electron microscopy) may be used to measure the maximum value for the step height h1 depending on the material (for example, silicone oil) of the insulating film 20.

Figure 3:
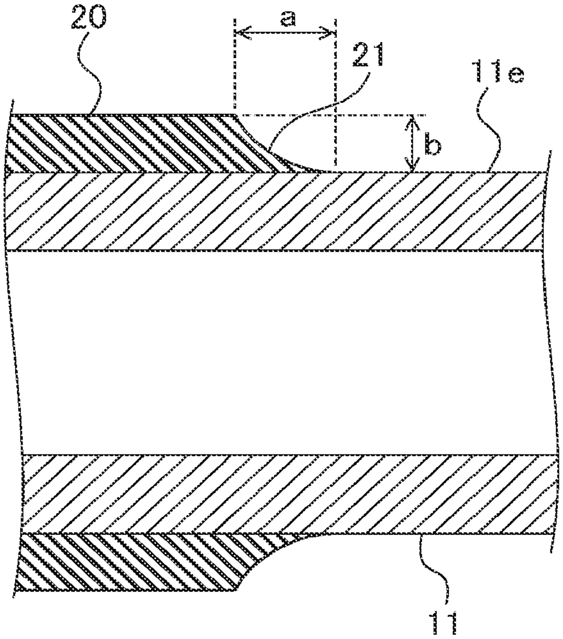
FIG. 3 is an enlarged cross-sectional view showing another example of a boundary between a shaft part and an end on a tip side of an insulating film in FIG. 1.

FIG. 3 is an enlarged cross-sectional view showing another example of the boundary between the shaft part 11 and the end on the tip side of the insulating film 20 in FIG. 1. At the end on the tip side of the insulating film 20, it preferably has a gradually decreasing part 21 for which the film thickness of the insulating film 20 gradually decreases toward the tip part 12. If the insulating film 20 has the gradually decreasing part 21, since the film thickness of the insulating film 20 gradually decreases toward the tip part 12 at the annular end of the insulating film 20, it is possible to smoothly insert the hollow needle 1 into a living body.

As shown in FIG. 3, in the case of having the gradually decreasing part 21 in which the film thickness on the tip side of the insulating film 20 gradually decreases toward the tip part 12, it may be a configuration without a step at the location where the outer circumferential surface 11*e* of the shaft part 11 and the gradually decreasing part 21 connect at the end position on the tip side of the insulating film 20. In the case of such a configuration, since there is no step at the connecting location, it is possible to insert the hollow needle 1 more smoothly into a living body. In addition, the slope of the gradually decreasing part 21 becomes smaller as the gradually decreasing ratio (b/a) of the gradually decreasing part 21 defined by the length (a) in the longitudinal direction of the gradually decreasing part 21 and the film thickness (b) of the insulating film 20 at the end position on the base end side of the gradually decreasing part 21 becomes smaller, and it is possible to smoothly insert the hollow needle 1 into a living body. At this time, when defining the angle formed by the tip 12*c* of the hollow needle 1 as θ as shown in FIG. 1, it is more preferable for the gradually decreasing ratio (b/a) of the gradually decreasing part 21 to be tan θ or less.

Figure 4:
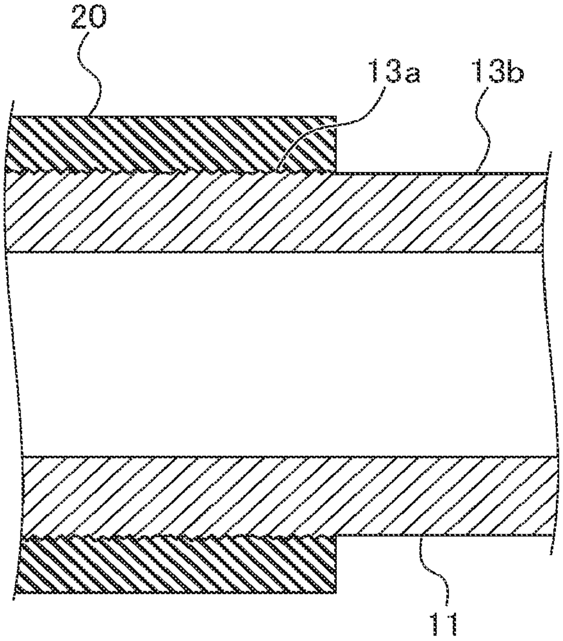
FIG. 4 is an enlarged cross-sectional view showing an example of a coated surface and an uncoated surface of a shaft part.

FIG. 4 is an enlarged cross-sectional view showing an example of the coated surface 13*a* and the uncoated surface 13*b* of the shaft part 11. The surface roughness Ra of the coated surface 13*a* of the shaft part 11 coated with the insulating film 20 is preferably more than 0 μm and 1 μm or less. For the coated surface 13*a*, the adhesion with the insulating film 20 is considered to become more favorable for a course state with large surface roughness Ra than a smooth state with small surface roughness Ra. If the surface roughness Ra of the coated surface 13*a* is more than 0 μm and 1 μm or less, roughening treatment of the shaft part 11 is easy. It should be noted that the surface roughness Ra is an arithmetic average roughness, and is based on JIS B 0601.

In the case of the coated surface 13*a* of the shaft part 11 being roughened within the above-mentioned range of surface roughness Ra, from the viewpoint of an adhesion improvement of the insulating film 20, at least part of the coated surface 13*a* is preferably roughened, and the entirety of the coated surface 13*a* is more preferably roughened as shown in FIG. 4. In the case of at least part of the coated surface 13*a* being roughened, if the tip part side of the coated surface 13*a* is roughened, it is possible to improve the adhesion of the insulating film 20 to the shaft part 11.

As shown in FIG. 4, the surface roughness Ra of the uncoated surface 13*b* of the shaft part 11 not coated with the insulating film 20 is preferably smaller than the surface roughness Ra of the coated surface 13*a* of the shaft part 11 coated with the insulating film 20. If the surface state of the uncoated surface 13*b* is smoother than the coated surface 13*a*, the adhesion of the insulating film 20 is favorable, and it is possible to smoothly insert the hollow needle 1 into a living body. In particular, when the surface on the tip side of the insulating film 20 is the uncoated surface 13*b* which is smoother than the coated surface 13*a* as shown in FIG. 4, it is possible to more smoothly insert the hollow needle 1 into a living body.

In the insulating film 20, the surface roughness Ra of an area abutting the coated surface 13*a* of the shaft part 11 coated with the insulating film 20 is preferably more than 0 μm and 1 μm or less. If the surface roughness Ra of this area of the insulating film 20 is within the above-mentioned range, the adhesion property of the insulating film 20 improves.

Next, a use example of the hollow needle 1 of the embodiment will be explained.

Figure 5:
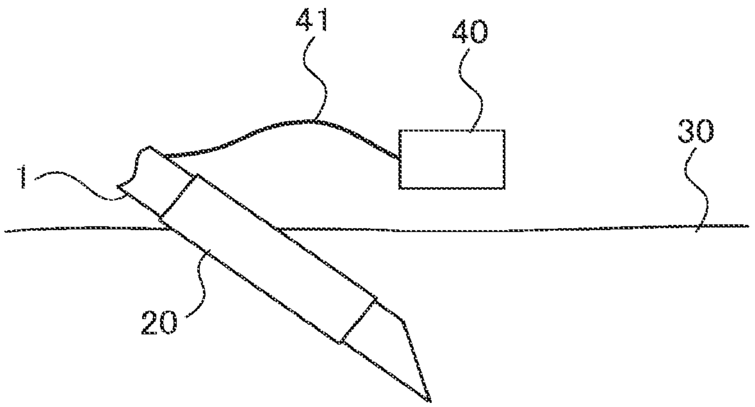
FIG. 5 is an outline drawing showing an example of a use example of the hollow needle according to the embodiment.

FIG. 5 is an outline drawing showing an example of a use example of the hollow needle 1. A detection device 40 for the hollow needle is connected to a portion of the shaft part 11 of the hollow needle 1 which is not covered by the insulating film 20, via a connection wire 41.

To the hollow needle 1 inserted into a living body 30, an electric signal is input via the connection wire 41 from a signal input unit provided to the detection device for the hollow needle. The electric signal inputted to the hollow needle 1 flows toward the tip part 12 from the shaft part 11 of the needle body 10. The electric signal does not flow to the insulating film 20. The electric signal flowing to the tip part 12 is received by a receiver provided to the detection device 40 for the hollow needle, as a position information of the tip part 12. For this reason, the detection precision of the tip part 12 of the hollow needle 1 is favorable. Then, the injection of a drug solution can be performed by the hollow needle 1 reaching the objective location.

Figure 6:
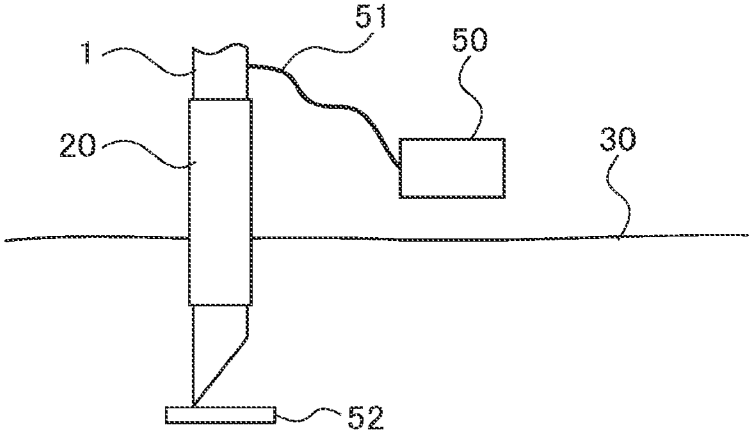
FIG. 6 is an outline drawing showing another example of a use example of the hollow needle according to the embodiment.

FIG. 6 is an outline drawing showing another example of a use example of the hollow needle 1. A detection device 50 for an implant device is connected to a portion of the shaft part 11 of the hollow needle 1 not covered by the insulating film 20, via a connection wire 51. An implant device 52 is installed in advance inside of the living body 30.

To the hollow needle 1 inserted in the living body 30, an electric signal is input via the connection wire 51 from the signal input unit provided to the detection device 50 for the implant device. The electric signal inputted to the hollow needle 1 flows from the needle body 10 toward the implant device 52. The electric signal flowed to the implant device 52 is received as a signal that the hollow needle 1 was contact with the implant device 52, by a receiver provided to the detection device 50 for implant device, via a transmitter provided to the implant device 52. For this reason, for the detection device 50 for implant device, the detection accuracy of contact between the hollow needle 1 and the implant device 52 becomes favorable. Then, the injection of a drug solution can be performed by the hollow needle 1 reaching the implant device 52. In addition, the hollow needle 1 is connected with a syringe via a predetermined connector (for example, connector of an international standard (ISO (IEC) 80369 series)).

Figure 7:
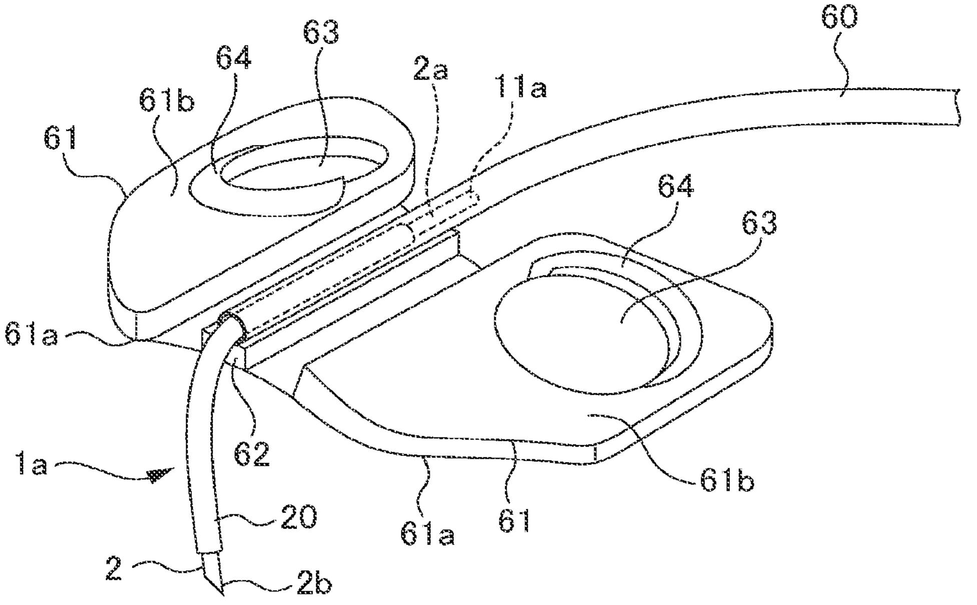
FIG. 7 is an outline drawing showing yet another example of a use example of the hollow needle according to the embodiment.

FIG. 7 is an outline drawing showing yet another example of a use example of the hollow needle. A hollow needle 1*a* shown in FIG. 7 is made by equipping the insulating film 20 to a Huber-pointed needle 2. The Huber-pointed needle 2 is configured so that a shaft part 2*a* slopes or bends toward a tip part 2*b*, and an opening forms at the tip part 2*b*. The Huber-pointed needle 2 is a dedicated needle for making the administration of cancer chemotherapy or high-calorie infusion via a subcutaneous embedded central venous port (CV port) implanted in the skin.

The Huber-pointed needle 2 has a shaft part 2*a* in which a base end 11*a* is inserted in a tube 60 through which a drug solution or the like flows, and which extends within a boundary part 62 of a pair of vane parts 61; and a tip part 2*b* bending and extending. Herein, a sequence when puncturing the Huber-pointed needle 2 to the skin will be explained. A practitioner pinches the vane parts 61 of the Huber-pointed needle 2 to bring together the top surfaces 61*b* to close. Next, the practitioner punctures the Huber-pointed needle 2 to the skin while maintaining this closed state. Then, the practitioner, after puncturing the Huber-pointed needle 2 to the skin, opens so that the bottom surfaces 61*a* of the vane parts 61 contact the skin in order to secure the fixing to the skin, and fixes the top surfaces 61*b* of the vane parts 61 to the skin with adhesive tape or the like. As the material constituting the vane part 61, silicone or the like can be exemplified considering the proper balance of strength and flexibility. In the pair of vane parts 61, the through holes 63 are provided at corresponding positions of each. Protrusions 64 inserting into the through hole 63 of each other upon closing the vane parts 61 are provided on the top surfaces 61*b* of the pair of vane parts 61. When respectively fitting each protrusion 64 to the through hole 63 of the other, it is possible to maintain the state in which the vane parts 61 are closed. When using such a hollow needle 1*a* together with the detection device 40 of FIG. 5 or the detection device 50 of FIG. 6, it is possible to precisely detect the tip part of the hollow needle 1*a* including the Huber-pointed needle 2, and possible to inject a drug solution from the hollow needle 1*a* having reached the desired location.

According to the above explained embodiment, in the hollow needle 1, the electric signal flows only to the needle body 10, without flowing to a portion of the insulating film 20 coating the shaft part 11. In addition, the hollow needle 1 charges the drug solution from the opening 11*b* of the base end 11*a* of the shaft part 11, and can inject the drug solution from the opening 16. In addition, the hollow needle 1 extracts the body fluid such as blood inside of the living body from the opening 16, and can extract the body fluid from the opening 11*b* of the base end 11*a* of the shaft part 11. For this reason, the hollow needle 1 having the needle body 10 and the insulating film 20 is able to deal with injection of a drug solution into a living body or extraction of a body fluid from inside a living body, and enables recognition of the position of the opening of the needle in the living body or the position of the tip from outside the living body.

It should be noted that the above-mentioned embodiment shows an example in which the tip 11*c* of the shaft part 11 and the base end 12*a* of the tip part 12 are integrally coupled, as shown in FIG. 1; however, the hollow needle 1 may include a cylindrical intermediate part (not shown) between the shaft part 11 and the tip part 12. In the case of the hollow needle 1 including the intermediate part, the base end of the intermediate part couples the tip 11*c* of the shaft part 11, the tip of the intermediate part couples to the base end 12*a* of the tip part 12, and the shaft part 11 couples to the tip part 12 via the intermediate part.

In addition, as shown in FIG. 3, although an example is shown in which the gradually decreasing part 21 of the insulating film 20 gradually decreases non-linearly with a concaved curved surface, the gradually decreasing part 21 of the insulating film 20 may gradually decrease non-linearly with a convex curved surface, or may gradually decrease linearly.

Figure 8:
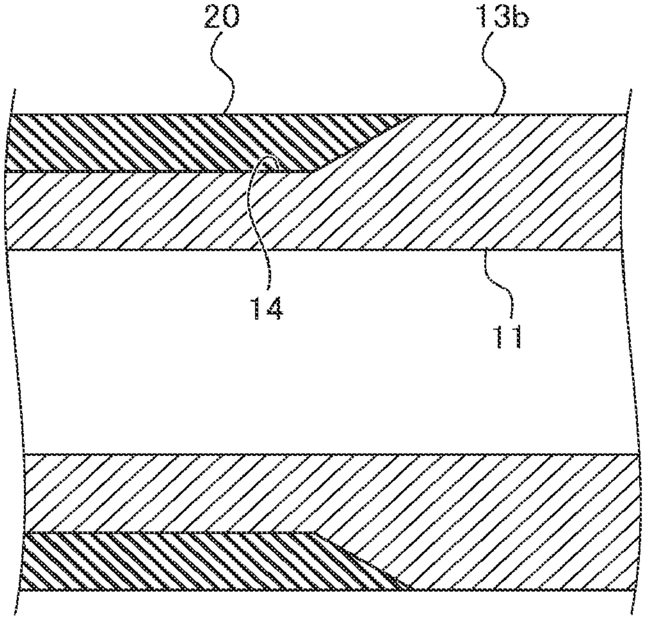
FIG. 8 is an enlarged cross-sectional view showing an example of a state of an insulating film which coats the shaft part of a needle body including a recessed part.

In addition, as shown in FIG. 8, the insulating film 20 may coat the shaft part 11 of the needle body 10 including the annular recessed part 14. With such a hollow needle 1, the needle body 10 includes an annular recessed part 14 with a decreased thickness on at least part of the outer circumferential surface 11*e* of the shaft part 11, and the insulating film 20 is accommodated in the recessed part 14 of the shaft part 11. The recessed part 14 is provided to the outer circumferential surface 11*e* of the shaft part 11, and decreases the thickness in the radial direction of the shaft part 11 from the outer circumferential side. The insulating film 20 accommodated in the recessed part 14 coats the outer circumferential surface of the shaft part 11 including the recessed part 14. For this reason, during insertion to a living body of the hollow needle 1, peeling of the insulating film 20 provided in the recessed part 14 is suppressed.

Figure 9:
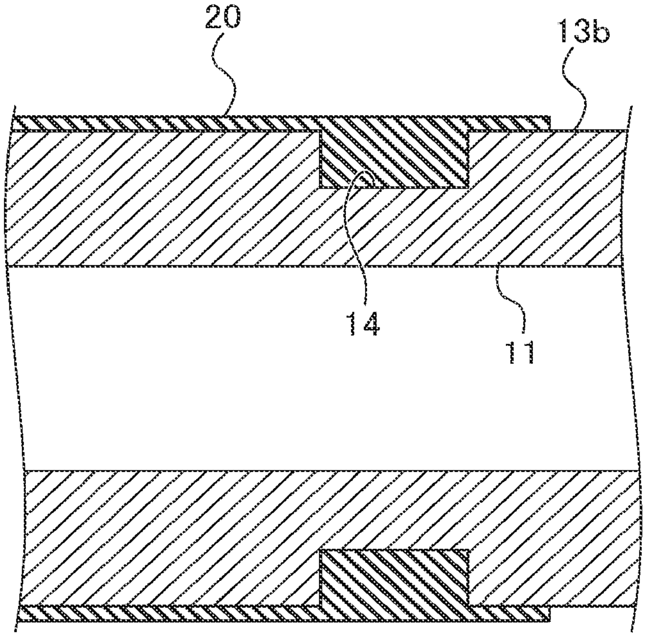
FIG. 9 is an enlarged cross-sectional view showing another example of a state of an insulating film which coats the shaft part of a needle body including a recessed part.
Figure 10:
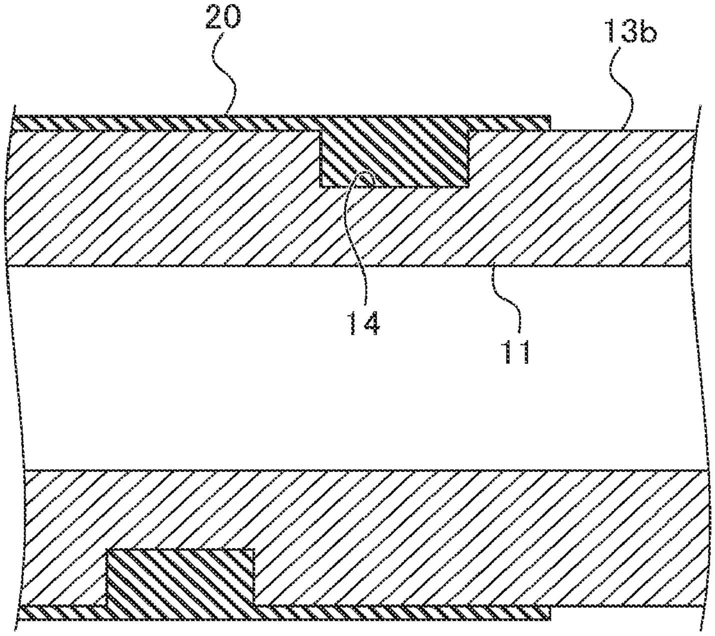
FIG. 10 is an enlarged cross-sectional view showing yet another example of a state of an insulating film which coats the shaft part of a needle body including a recessed part.

In addition, the recessed part 14 may not necessarily be annular. For example, as shown in FIGS. 9 and 10, the recessed part 14 may be provided on part of the outer circumferential surface of the shaft part 11. In FIG. 9, two of the recessed parts 14 are provided at the same position in the longitudinal direction, and in FIG. 10, two of the recessed parts 14 are provided at different positions in the longitudinal direction. In addition, in FIGS. 9 and 10, the angle formed by the bottom surface and the side surface of the recessed part 14 is 90 degrees; however, this formed angle may be more than 90 degrees and less than 180 degrees, as shown in FIG. 8. If this formed angle is more than 90 degrees and less than 180 degrees, it is possible to more smoothly insert the hollow needle 1 into a living body.

Figure 11:
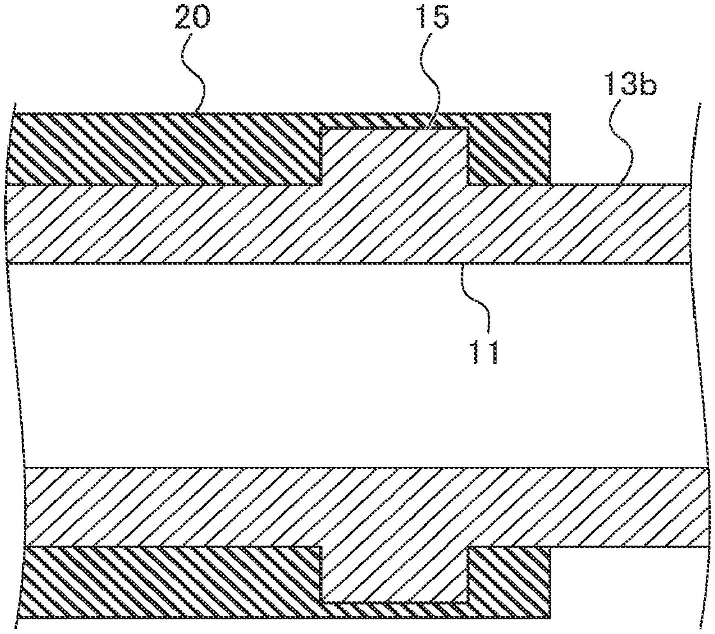
FIG. 11 is an enlarged cross-sectional view showing an example of a state of an insulating film which coats the shaft part of a needle body including a convex part.
Figure 12:
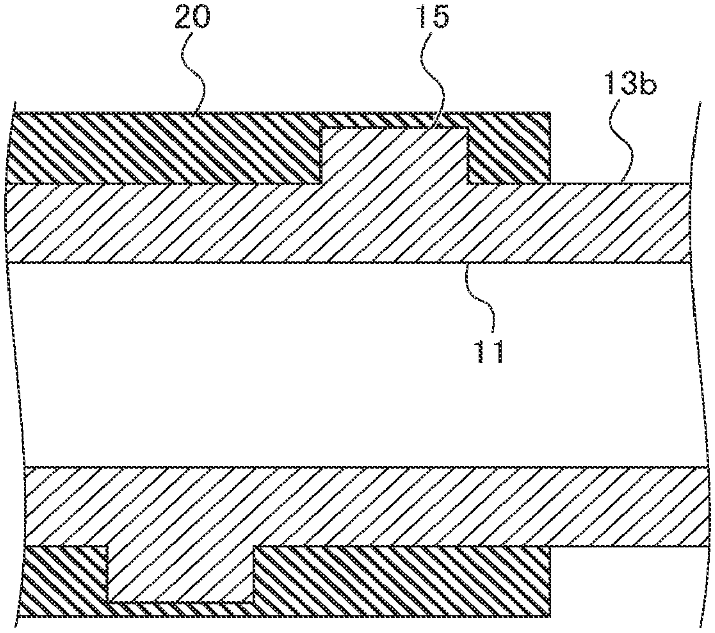
FIG. 12 is an enlarged cross-sectional view showing another example of a state of an insulating film which coats the shaft part of a needle body including a convex part.

In addition, as shown in FIGS. 11 and 12, the insulating film 20 may coat the shaft part 11 of the needle body 10 including a convex part 15. The convex part 15 is provided to the outer circumferential surface of the shaft part 11. The insulating film 20 coats the outer circumferential surface of the shaft part 11 including the convex part 15. For this reason, during insertion to the living body of the hollow needle 1, peeling of the insulating film 20 provided on the convex part 15 is suppressed. In FIG. 11, two of the convex parts 15 are provided at the same position in the longitudinal direction, and in FIG. 12, two of the convex parts 15 are provided at different positions in the longitudinal direction. In addition, in FIGS. 11 and 12, the angle formed by the top face and the side face of the convex part 15 is 90 degrees; however, this formed angle may be more than 90 degrees and less than 180 degrees. If this formed angle is more than 90 degrees and less than 180 degrees, it is possible to more smoothly insert the hollow angle 1 into a living body.

Figure 13:
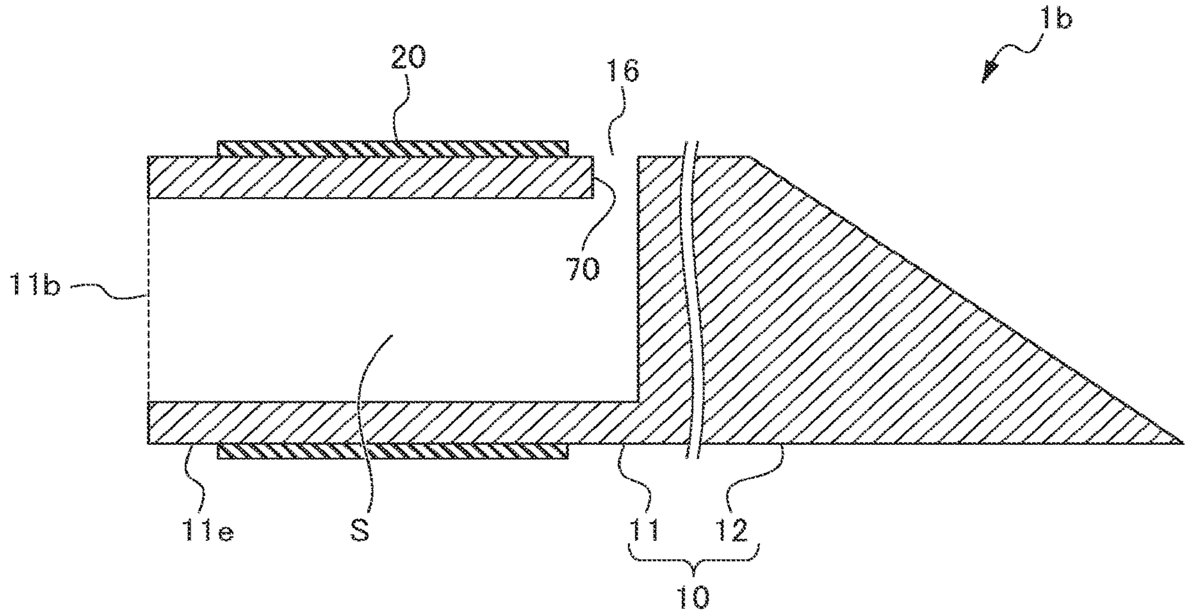
FIG. 13 is a longitudinal sectional view showing another example of a hollow needle according to an embodiment.

In addition, FIG. 1 shows an example in which the opening 16 is provided to a side of the tip 12*c* of the tip part 12; however, the opening 16 may be provided to an outer circumferential surface 11*e* of the shaft part 11, as shown in FIG. 13. In this case, a cavity S of the hollow needle 1*b* is not formed in the tip part 12, and only formed in the shaft part 11. A through hole 70 penetrating in the radial direction is provided to the shaft part 11. The cavity S provided inside of the needle body 10 communicates from the opening 11*b* of the base end 11*a* of the shaft part 11 until the opening 16 via the through hole 70.

Although an embodiment has been explained above, the present invention is not to be limited to the above-mentioned embodiment, and includes any mode encompassed by the gist and claims of the present disclosure, and can be modified in various ways within the scope of the present disclosure.

EXPLANATION OF REFERENCE NUMERALS

1, 1*a*, 1*b* hollow needle
2 Huber-pointed needle
2*a* shaft part
2*b* tip part
10 needle body
11 shaft part
11*a* base end of shaft part
11*b* opening at base end of shaft part
11*c* tip of shaft part
11*d* opening at tip of shaft part
11*e* outer circumferential surface of shaft part
12 tip part
12*a* base end of tip part
12*b* opening at base end of tip part
12*c* tip of tip part
13*a* coated surface
13*b* uncoated surface
14 recessed part
15 convex part
16 opening
20 insulating film
21 gradually decreasing part
30 living body
40 detection device for hollow needle
41 connection wire
50 detection device for implant device
51 connection wire
52 implant device
60 tube
61 vane part
61*a* bottom of vane part
61*b* top surface of vane part
62 boundary part
63 through hole
64 protrusion
70 through hole
S cavity

The invention claimed is:

1. A hollow needle comprising:

a needle body made of an electrically conductive material, forming a cylindrical shape, and including a shaft part, a tip part connected with the shaft part, and an opening for discharging or drawing in a liquid, wherein a cavity communicating between the shaft part and the opening is formed inside; and an annular insulating film made of an electrically insulative material, which exposes the opening and at least part of the tip part, and coats at least part of an outer circumferential surface of the shaft part;

at an end on a side of a tip part of the insulating film, a gradually decreasing part for which a film thickness of the insulating film gradually decreases toward the tip part.

2. The hollow needle according to claim 1, wherein at least part of an outer circumferential surface of the tip part is electrically conductive, and is electrically connected to the shaft part.

3. The hollow needle according to claim 1, wherein a maximum value for a step height h1 from the outer circumferential surface of the shaft part until a surface of the insulating film at an end position on a side of the tip part of the insulating film is 200 μm or less.

4. The hollow needle according to claim 1, wherein the needle body includes a recessed part with a decreased thickness on at least part of the outer circumferential surface of the shaft part, and wherein the insulating film is accommodated in the recessed part of the shaft part.

5. The hollow needle according to claim 1, wherein a surface roughness Ra of a coated surface of the shaft part which is coated with the insulating film is more than 0 μm and 1 μm or less.

6. The hollow needle according to claim 1, wherein a surface roughness Ra of an uncoated surface of the shaft part which is not coated with the insulating film is smaller than a surface roughness Ra of the coated surface of the shaft part which is coated with the insulating film.

7. The hollow needle according to claim 1, wherein the shaft part slopes or bends toward the tip part, and the opening is formed at the tip part.

8. The hollow needle according to claim 1, wherein the insulating film is configured from a resin having an electrical insulating property.

9. The hollow needle according to claim 1, wherein the insulating film is configured from a polyimide resin or a fluorocarbon resin.

10. The hollow needle according to claim 1, wherein the needle body is configured from a metal.

11. The hollow needle according to claim 1, wherein the needle body is configured from a stainless steel, a titanium alloy or a cobalt/molybdenum-containing alloy.

12. The hollow needle according to claim 2, wherein a maximum value for a step height h1 from the outer circumferential surface of the shaft part until a surface of the insulating film at an end position on a side of the tip part of the insulating film is 200 μm or less.

13. The hollow needle according to claim 2, further comprising, at an end on a side of the tip part of the insulating film, a gradually decreasing part for which a film thickness of the insulating film gradually decreases toward the tip part.

14. The hollow needle according to claim 2, wherein the needle body includes a recessed part with a decreased thickness on at least part of the outer circumferential surface of the shaft part, and wherein the insulating film is accommodated in the recessed part of the shaft part.

15. The hollow needle according to claim 2, wherein a surface roughness Ra of a coated surface of the shaft part which is coated with the insulating film is more than 0 μm and 1 μm or less.

16. The hollow needle according to claim 2, wherein a surface roughness Ra of an uncoated surface of the shaft part which is not coated with the insulating film is smaller than a surface roughness Ra of the coated surface of the shaft part which is coated with the insulating film.

17. The hollow needle according to claim 2, wherein the shaft part slopes or bends toward the tip part, and the opening is formed at the tip part.

18. The hollow needle according to claim 2, wherein the insulating film is configured from a resin having an electrical insulating property.

19. The hollow needle according to claim 2, wherein the insulating film is configured from a polyimide resin or a fluorocarbon resin.

* * * * *